United States Patent
Rosso et al.

(10) Patent No.: US 6,968,037 B2
(45) Date of Patent: Nov. 22, 2005

(54) HIGH THROUGHPUT X-RAY DIFFRACTION FILTER SAMPLE HOLDER

(75) Inventors: Victor W. Rosso, East Windsor, NJ (US); Glen Young, New Brunswick, NJ (US); Joseph Nolfo, Hawthorne, NJ (US); Imre M. Vit z, Whitehouse Station, NJ (US); John J. Venit, New Brunswick, NJ (US)

(73) Assignee: Bristol-Myers Squibb Co., Princeton, NJ (US)

( * ) Notice: Subject to any disclaimer, the term of this patent is extended or adjusted under 35 U.S.C. 154(b) by 135 days.

(21) Appl. No.: 10/410,910

(22) Filed: Apr. 10, 2003

(65) Prior Publication Data

US 2004/0028179 A1 Feb. 12, 2004

Related U.S. Application Data

(60) Provisional application No. 60/371,550, filed on Apr. 10, 2002.

(51) Int. Cl.$^7$ .............................................. G01N 23/20
(52) U.S. Cl. ......................................... 378/79; 378/71
(58) Field of Search ..................... 378/70–79; 436/178; 359/819

(56) References Cited

U.S. PATENT DOCUMENTS

| | | | |
|---|---|---|---|
| 4,278,883 A | | 7/1981 | Hathaway et al. ............. 378/79 |
| 4,797,260 A | * | 1/1989 | Parker ......................... 422/101 |
| 5,244,858 A | | 9/1993 | Usui et al. .................... 502/220 |
| 5,351,281 A | * | 9/1994 | Torrisi et al. .................. 378/79 |
| 5,390,230 A | * | 2/1995 | Chang .......................... 378/80 |
| 5,792,430 A | * | 8/1998 | Hamper ....................... 422/131 |
| 6,677,162 B1 | * | 1/2004 | Wendelbo et al. ........... 436/174 |
| 2003/0068829 A1 | * | 4/2003 | Giaquinta et al. ........... 436/173 |
| 2004/0168529 A1 | * | 9/2004 | Carlson et al. ................ 73/866 |

FOREIGN PATENT DOCUMENTS

| | | |
|---|---|---|
| WO | WO 01/51919 A3 | 7/2001 |
| WO | WO 01/82659 A1 | 11/2001 |
| WO | WO 03/050598 A2 | 6/2003 |

\* cited by examiner

*Primary Examiner*—Craig E. Church
*Assistant Examiner*—Jurie Yun
(74) *Attorney, Agent, or Firm*—Deanna L. Baxam

(57) ABSTRACT

Multiple samples are prepared in slurry form and deposited through a funnel plate by a multiprobe liquid handler into an array of inserts situated in openings in a housing. Each insert has a recess that extends through the insert body and a filter disc situated in the recess to support the sample. The filter is held in place by an annular part which defines a channel providing access to the filter through the lower portion of the recess. A pressure differential is created across each of the filters by attaching a vacuum manifold to the bottom of the housing to simultaneously remove the liquid from each of the samples, leaving the samples in powder form. The housing is then placed in the X-ray diffractometer for sequential analysis of each of the samples, while the samples are situated in the inserts.

34 Claims, 4 Drawing Sheets

HIGH THROUGHPUT X-RAY DIFFRACTION FILTER SAMPLE HOLDER

This application claims a benefit of priority from U.S. Provisional Application No. 60/371,550, filed Apr. 10, 2002, the entire disclosure of which is herein incorporated by reference.

The present invention relates to systems for analyzing the crystalline physical and chemical forms of pharmaceutical compounds, and more specifically to a filtration sample holder for use in powder X-ray diffraction analysis that facilitates the isolation and testing of small amounts of multiple pharmaceutical compound samples by virtually eliminating the manual handling of the samples, thus reducing sample loss and increasing throughput.

As used in this specification, the term "pharmaceutical compound(s)" should be construed broadly to include any organic or inorganic molecule that may be crystalline. With respect to pharmaceutical research, this includes but is not limited to any active pharmaceutical ingredient (API), final intermediate (AKA penultimate intermediate), pivotal intermediate, isolated intermediate, protein, deoxyribonucleic acid (DNA), ribonucleic acid (RNA), amino acid, polypeptide, fermentation product, complex and starting material, regardless of its source (natural, unnatural or semi-synthetic). "Pharmaceutical compound(s)" includes the colloquial references including but not limited to large molecules, small molecules, neutral molecules, semi-synthetic molecules, or biological (or fermentation) molecules. It also includes any compound that may be used in the synthesis of a pharmaceutical.

Potential drug candidates include organic and inorganic molecules, which may crystallize in one of several different forms, or a mixture of these forms. Different physical (polymorphs) and chemical (salt forms, solvates, and complexes) forms of a compound can have significantly different physiochemical properties. In some instances, the different physicochemical properties (e.g. solubility, melting point, etc.) can lead to differences in bioavailability in preclinical and clinical testing.

The crystallization parameters that influence the solid state form of any compound include temperature, reaction time, pH, concentration of the compound of interest in a solvent or solvents and concentration of impurities in a solvent or solvents. Additional crystallization parameters that influence the solid state form of any compound include seeding or lack thereof, nucleation rate, precipitation rate, crystallization rate, saturation point, and solubility with respect to temperature. Additionally, the rate of adjustment of any or all of the aforementioned parameters, as well as the type and composition of the solvent used, will influence the solid state form. Henceforth, the polymorphs, solvates, complexes and salt forms of compounds will be referred to as "forms" for simplicity.

Identification of an optimal form of a compound is one of the key requirements for successful pharmaceutical development. If a mixture of forms is produced, the ratio of the different forms must be predictable within certain limits. Further, it is important to determine which polymorph form of the compound is produced by a particular set of parameters in order to formulate the optimum protocol for producing the compound. It is therefore critical to have a means of isolating, washing and analyzing arrays of solids for their crystalline properties.

One common diagnostic method for identifying the crystalline forms of a compound is by X-ray diffraction. Because the atomic coordinates of each polymorph are different, its crystal will diffract X-rays in a distinctive pattern. Typically, the samples screened in pharmaceutical development are a collection of randomly oriented crystallites that form a powder. For that reason, the technique is often referred to as powder X-ray diffraction.

The X-ray diffraction from a crystalline powder sample generates a certain pattern. Typical powder X-ray diffraction instruments designed for laboratory use are capable of measuring a powder diffraction pattern from approximately 100–500 mgs of material. The pattern is measured by scanning a sample with an X-ray beam and at the same time scanning a detector that measures the intensity of radiation diffracted by the sample as a function of the diffracting angle.

The pattern of the diffracted radiation received at the detector is characteristic of the sample. Since each crystalline structure dictates a unique pattern, it is possible to identify which form of the compound is present in the sample by analyzing the diffraction pattern.

Often, several different polymorphs of a compound are produced. It is important to test a variety of crystallization conditions to ensure that all polymorphs that can be produced are identified, and to optimize the crystallization conditions which produce the polymorphs with the best therapeutic properties. This may require that large numbers of samples be screened. Screening of large numbers of samples using X-ray diffraction equipment can best be accomplished by automating the analysis system.

The present invention relates to a unique filtration sample holder for powder X-ray diffraction analysis. The sample holder facilitates the screening of large numbers of samples in powder form while virtually eliminating the manual handling of the samples to be screened, and thus also eliminating the loss of sample which accompanies such handling. Moreover, the sample holder permits analysis of amounts of the sample that are smaller than normally possible with conventional laboratory powder X-ray diffraction equipment.

The use of the filtration sample holder according to the invention results in a high throughput automated powder X-ray diffraction analysis system capable of identifying which forms of a potential drug candidate have been produced by a particular set of production parameters. This leads to the optimization of the production protocol for producing the form of the compound with the best therapeutic properties.

Samples of the compounds to be tested are produced in slurry form. The liquid must be removed from the slurry to obtain the compound in a powder form suitable to be tested. In the laboratory procedure commonly used, conventional filtration equipment is employed to remove the liquid from the slurry for each compound to be tested. The remaining powder of each sample is then transferred to a container, such as a bottle. Information as to the procedure by which the compound was produced is entered into a database and matched with the container. Although efficient for the analysis of single samples, this procedure rapidly becomes tedious when multiple samples are analyzed.

The containers are collected and moved to the site of the X-ray diffraction equipment. The powder sample from each of the containers is removed from its container and placed in a X-ray sample holder. The sample holders are then mounted on the X-ray diffraction equipment. The resulting patterns are analyzed by computer, using the previously entered laboratory data.

The invention improves upon this process by virtually eliminating the manual handling of the samples. It reduces the tedium inherent in the filtration of multiple samples using conventional equipment designed to handle one sample at a time. The quantity of the samples which are normally lost by transferring samples from the filtration equipment to the containers, and from the containers to the sample holders is reduced, permitting smaller amounts of the samples to be produced for testing. It reduces worker exposure associated with handling potent or cytotoxic substances in powder form. It also eliminates the possibility of contamination from unsterilized containers or transfer equipment. All of this is accomplished by using a single piece of equipment for filtration and for holding the samples for X-ray diffraction analysis.

Further, the structure of the filtration sample holder of the invention permits smaller quantities of samples to be tested. The sample holder includes an insert, which is preferably cylindrical, that is designed to be received in a generally circular shaped opening in a housing. The housing can have a single opening for analyzing one compound at a time. However, more commonly, the housing will have an array of openings permitting the automated analysis of multiple compounds in sequence. The housing includes magnetic material or other means of interacting with sensors in the X-ray diffractometer that permits the X-ray diffractometer to detect the presence of the housing and perform the analysis on each sample in the housing. Alternatively, a system using two-dimensional X-Y or Cartesian coordinates may be incorporated to allow detection and analysis of the samples in the housing.

Each insert has a recess which extends through the insert. The recess is divided into upper and lower sections. A glass filter disc is situated in the lower section, at a location adjacent to the upper section, so as to form the floor of the upper section. The sample in slurry form is deposited in the upper, sample receiving section of the recess, preferably by a syringe or a liquid handler.

Filtration of the samples takes place simultaneously, while the inserts are located in the housing, eliminating the need to handle the samples and the inherent sample loss. A pressure differential is created across each filter by applying either pressure or a vacuum. Preferably, a vacuum is connected to the bottom surface of the filter through the lower section of the recess of each insert. The liquid in each slurry is removed through the filter, leaving the sample in powder form in a thin layer on the upper surface of the filter. The samples are washed and dried and thus made ready for analysis.

The shape and size of the sample retaining recess section is selected to accommodate the minimal sample size required to produce an acceptable quality X-ray diffraction spectra. Thus, very small sample quantities can be tested.

The housing, with the inserts, is then placed into the X-ray diffraction equipment, which detects the presence of the housing using orientation or magnetic sensing means. X-rays are directed at each sample in turn, while the samples remain in the sample receiving sections of the insert recesses. The X-ray diffraction pattern of each sample is then analyzed.

Since the loss of sample material which normally results from the transfer of the powder sample from the filtration equipment into a container and then from the container into the sample holder is eliminated, smaller quantities of the samples of the compounds to be tested need to be produced. Moreover, less handing results in better efficiency and hence higher throughput.

PCT International Publication Number WO 01/82659 A1, dated Nov. 1, 2001 and entitled, "System and Methods For High Throughput Screening of Polymorphs" and PCT International Publication Number WO 01/51919 A3, dated Jan. 8, 2001 and entitled, "High-Throughput Formation, Identification, and Analysis of Diverse Solid-Forms" provide background information relating to systems for the automated screening of compounds by X-ray diffraction. Those references differ from the present invention in that they teach only individual preparation of samples for X-ray diffraction analysis, not procedures that can be used in preparation of multiple samples. Further, neither reference teaches the use a filtration sample holder having a structure similar to the present invention, or which provides its advantages.

U.S. Pat. No. 4,278,883 issued to Hathaway et al. on Jul. 14, 1981, and entitled "Sample Mount for X-Ray Diffraction" teaches a solid body insert that supports a filter. The insert is designed to be received in a sample mount used for X-ray diffraction. However, compared to the present invention, the Hathaway insert has a very different structure and is designed for an entirely different purpose. The Hathaway equipment is used for filtering water samples collected at sea and analyzing the sediment, for example talc, by X-ray diffraction. The sample being analyzed is a suspension of a solid in water. The sample contains a small amount of solid in a large amount of water. Because of that, Hathaway's filter requires repeated loading in order to obtain enough solid for analysis.

Hathaway teaches the use of a filter made of silver. At the time of repeated loading of the filter, the filter is situated on a conventional laboratory filtration unit. After filtration has taken place, the solid remains on the surface of the filter. The filter is then removed from the filtration unit and placed on the top surface of the solid insert body. The insert is placed in the opening of the mount from underneath. The insert is held so it does not fall out of the mount by adhesive tape.

Because Hathaway's insert body is solid in the area below the filter, filtration of the sample cannot take place while the filter is situated in the insert, as is the case with our invention. Further, in Hathaway's insert, there is no recess section capable of receiving the sample in slurry form, prior to filtration. The Hathaway merely provides a surface for transferring the already filtered solid sample to the sample holder.

It is, therefore, an object of the present invention to provide a filter sample holder which increases the throughput of a X-ray diffraction analysis system.

It is another object of the present invention to provide a high throughput X-ray diffraction filter sample holder in which sample loss by manual handling of the samples in powder form from the filtration apparatus to the X-ray diffraction sample holder is eliminated.

It is another object of the present invention to provide a high throughput X-ray diffraction filter sample holder that includes an insert with a recess having a section for retaining a sample in slurry form.

It is another object of the present invention to provide a high throughput X-ray diffraction filter sample holder in which the sample retaining recess section is sized and shaped to permit analysis of smaller sample quantities.

It is another object of the present invention to provide a high throughput X-ray diffraction filter sample holder that includes an insert with a filter, where the filter forms the floor of a sample receiving recess.

It is another object of the present invention to provide a high throughput X-ray diffraction filter sample holder including a housing for carrying the sample containing inserts that interacts with a X-ray diffractometer.

It is another object of the present invention to provide a high throughput X-ray diffraction filter sample holder in which the housing has openings for receiving one or more sample containing inserts.

It is another object of the present invention to provide a high throughput X-ray diffraction filter sample holder in which the filter in the insert can be operably connected to equipment for creating a pressure differential across the filter to remove the liquid portion of the sample containing slurry, while the insert is in the housing.

It is another object of the present invention to provide a high throughput X-ray diffraction filter sample holder in which the samples in multiple inserts can be analyzed sequentially in an X-ray diffractometer, in an automated fashion.

It is another object of the present invention to provide apparatus for the introduction and filtration of samples of multiple pharmaceutical compounds in an array of X-ray diffraction filter sample inserts situated in a housing including a funnel plate and a vacuum plate.

In accordance with one aspect of the present invention, a process for the X-ray analysis of a compound is provided. The process begins with the preparation of a sample of the compound to be analyzed in slurry form. The sample containing slurry is transferred to an assembly for X-ray diffraction analysis. The assembly includes a housing with an opening and an insert. The insert is received in the housing opening. The insert has a recess for receiving the sample in slurry form and a filter situated in the recess. The filter supports the sample. While the insert is in the housing opening, a pressure differential is created across the filter to remove the liquid portion of the slurry through the filter, leaving the sample to be analyzed in the powder form in the insert recess. The assembly is transferred into a X-ray diffractometer. The X-ray diffraction analysis is performed on the sample while the sample is in the insert recess.

The step of transferring the sample containing slurry includes the step of introducing the compound containing slurry into the insert recess. This may be accomplished using a funnel and a syringe or a liquid handler.

The step of creating the pressure differential includes applying a vacuum to the filter by connecting a vacuum to the filter, through the insert recess.

The step of receiving the insert in the housing opening includes the step of placing the insert into the housing opening from above the upper surface of the housing. The step of placing the insert includes the step of seating the insert within the opening. The insert has a radially extending flange which cooperates with the housing to properly position the insert.

In accordance with another aspect of the present invention, an automated process for the X-ray diffraction analysis of multiple compounds is provided. The process begins with the preparation of a sample of each of the multiple compounds to be analyzed in slurry form. The samples may be prepared as an array in a multi-well reactor using a suitable chemical reaction process. Non-limiting examples of such reaction processes include crystallization, precipitation, salt formation, and any other means of obtaining solid samples from a solution or reaction mixture. Each sample-containing slurry is transferred to an assembly for retaining X-ray diffraction analysis samples. The assembly includes a housing with an array of openings. Multiple inserts, one for each sample, are received in the housing openings. Each insert has a recess for receiving a sample in slurry form and a filter. The filter supports the sample. While the inserts are in the housing, a pressure differential is created across each filter to remove the liquid portion of each slurry, leaving each sample to be analyzed in powder form in the insert recess. The assembly, with the sample containing inserts, is transferred to a X-ray diffractometer. X-ray analysis is performed on each sample, in sequence, while the samples are situated in the insert recesses.

The step of transferring the sample includes the step of introducing each of the multiple samples in slurry form into the recess into one of a plurality of X-ray diffraction analysis sample assembly inserts. The step of introducing each of the multiple samples in slurry form includes the step of depositing each of the multiple samples in slurry form with an automated liquid handler. This is preferably accomplished through a funnel plate.

The step of creating a pressure differential includes the step of applying a vacuum to each filter by simultaneously applying a vacuum to the filter in each insert, through the recess in each insert. This is accomplished using a multi-port vacuum plate beneath the housing.

The process further includes the steps of generating laboratory information data for each of the multiple samples to be analyzed. The data is utilized in the X-ray diffraction analysis.

In accordance with another aspect of the present invention, an insert is provided for use in an X-ray diffraction sample housing. The housing has an opening for receiving the insert. The insert includes a recess which extends through the insert and a filter. The recess receives a sample of the compound to be analyzed in slurry form. Means are provided for retaining the filter in the recess to support the sample.

The recess has a first section into which the sample is received. The recess has a second section within which the filter is retained. The filter retaining means has a channel providing access to the filter, through the recess.

The insert is designed for use with vacuum means. The vacuum means is connected to the filter, through the channel, to remove the liquid from the slurry, while the sample is in the insert.

The insert is preferably generally cylindrical in shape. The filter is preferably disc shaped.

In accordance with another aspect of the present invention, a X-ray diffraction analysis filtration sample assembly is provided including an insert and a housing with an opening for receiving the insert. The insert has a recess and a filter. The recess extends through the insert. The recess receives a sample of the compound to be analyzed in the form of a slurry. Means are provided for retaining the filter in the recess to support the sample.

The filter retaining means includes a channel. The channel provides access to the filter through the recess.

The assembly is used with means for creating a pressure differential across the filter. The means preferably take the form of vacuum means. The vacuum means is connected to the filter, through the channel, to remove the liquid from the slurry.

The recess has first section which receives the sample. It has a second section within which the filter is retained.

The insert receiving opening in the housing extends through the housing. The insert includes means for cooperating with the housing to position the insert within the housing opening. The cooperating means comprises a flange on the insert. The flange cooperates with means on the housing to properly seat the insert.

As discussed previously, the housing includes means for interacting with an X-ray diffractometer. This permits the X-ray diffractometer to detect the presence of the housing.

The elements of the device may vary in size, shape and configuration, however the insert is preferably cylindrical. Each insert recess is also preferably cylindrical. The housing is preferably annular. The filter is preferably disc shaped. The filter retaining means preferably has an annular configuration.

In accordance with another aspect of the present invention, an apparatus is provided for automated X-ray diffraction analysis of multiple compounds. The apparatus includes multiple inserts and a housing with an array of openings into which the inserts are received. Each insert has a recess which extends through the insert and a filter. Each recess receives a sample of the compound to be analyzed in slurry form. Means are provided for retaining the filter in the recess to support the sample. The housing is adapted to be received in an X-ray diffractometer.

Each insert recess has a section for receiving the sample. It also has a second section within which the filter is retained.

Automated liquid handler means are employed for introducing the compounds in slurry form into the sample receiving recess section of each of the inserts.

The apparatus further includes funnel means for facilitating the introduction of the compounds in slurry form into the recesses.

The filter retaining means defines a channel. The channel provides access to the filter through the second recess section.

The apparatus also includes means for simultaneously removing the liquid portion of the slurry from each of the inserts, through the filter, leaving the samples in powder form in the sample receiving recess section of each insert. The liquid portion removing means includes means for creating a pressure differential across each filter. These means preferably take the form of vacuum means. The vacuum means is operably connected to the filter in each insert through the second recess section of the insert.

The vacuum means includes a vacuum manifold. The manifold has a plurality of vacuum ports. A sealing ring is associated with each port. Each of the sealing rings aligns with and abuts a different one of the inserts.

The X-ray diffractometer has means for analyzing the structure of the sample in the receiving recess section of each of the inserts in the housing, in sequence. The sequential analysis means includes means for moving the housing relative to the X-ray diffractometer to align each of the inserts with the diffractometer, in sequence.

The apparatus includes means for generating data representative of each retained compound. The data is transferred to the X-ray diffractometer.

In accordance with another aspect of the present invention, apparatus is provided for the introduction and filtration of an array of samples of multiple compounds onto an array of X-ray diffraction analysis filter sample inserts. Each insert includes a recess which extends through the insert and a filter. The filter is situated in the recess and supports the sample. The apparatus includes a housing adapted to be received in a X-ray diffractometer. The housing has a plurality of openings into which the inserts are received. A funnel plate is situated above the housing. The funnel plate has a plurality of funnel shaped recesses each of which is aligned with the recess of a different one of the inserts. A vacuum plate is located below the housing. The vacuum plate includes a plurality of ports. Each of the ports is aligned with the recess of a different one of the inserts. Means are provided for connecting the ports to a vacuum source.

Means are provided for introducing a different one of the samples into each of the funnel shaped recesses in the funnel plate. The introduction means preferably comprises a multi-probe liquid handler.

The vacuum plate includes a plurality of sealing rings. Each sealing ring is received into a different one of the vacuum plate ports. Each of the sealing rings aligns with and abuts a different one of the inserts. More specifically, each of the sealing rings aligns with and abuts the filter retaining means of a different one of the inserts.

The housing includes means for interacting with a X-ray diffractometer. This enables the X-ray diffractometer to detect the presence of the housing.

To these and to such other objects which may hereinafter appear, the present invention relates to a high throughput X-ray diffraction filter sample holder, as set forth in detail in the following specification, and recited in the annexed claims, taken together with the accompanying drawings, in which like numerals refer to the like parts and in which:

Figure 1:
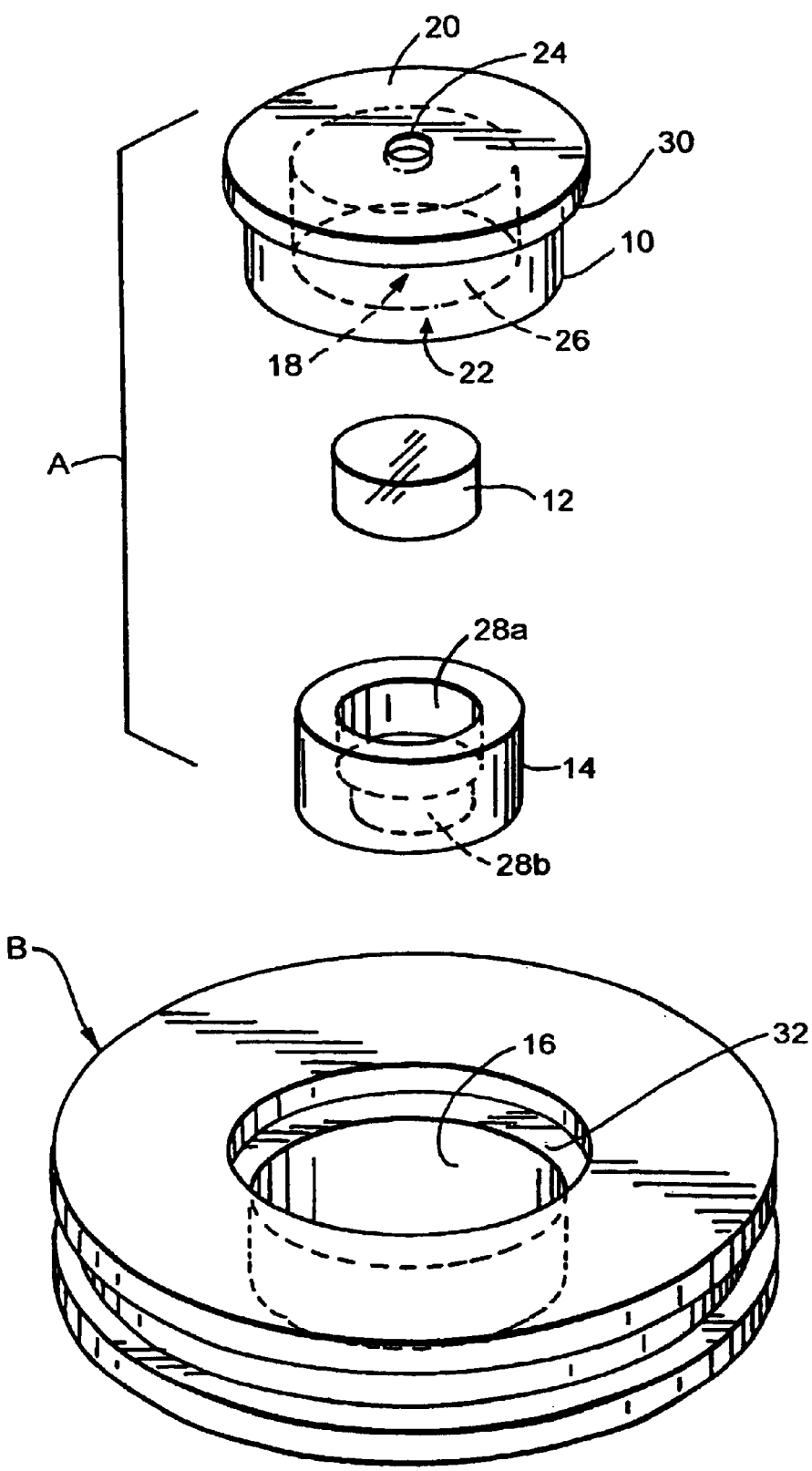
FIG. 1 is an exploded isometric view of an insert and a single insert housing.

FIG. 1 illustrates a first preferred embodiment of the sample holder of the present invention which takes the form of an insert and a single insert housing for use therewith. The insert is generally designated A. The housing is generally designated B. Together, insert A and holder B form an assembly for receiving a sample of a compound to be tested in slurry form, filtering the slurry to remove the liquid portion of the slurry, leaving the sample in powder form, and for holding the sample in powder form for analysis in a X-ray diffractometer.

Insert A consists of an insert body 10, a glass filter 12 and a filter retaining part 14. Insert A is designed to be received in opening 16 in housing B. Housing B is composed of a magnetic material such as steel. The housing is made of magnetic material so its presence can be detected by a sensor in the X-ray diffractometer. The X-ray diffractometer will not function unless the housing is detected in proper position in the machine.

Insert body 10 is generally cylindrical and is made of a corrosion resistant material such as monel, hastelloy or stainless steel. It has a recess 18 that extends through the insert body, from its upper surface 20 to its lower surface 22. Recess 18 includes a relatively small, shallow, upper section 24 into which a sample of the compound to be analyzed is received in slurry form. The slurry may be deposited into recess section 24 from above, using a funnel and a syringe. The lower section 26 of recess 18 is much larger in diameter and deeper than upper recess section 24.

Filter 12 is preferably a glass filter disc such as is commercially available from Ace Glass Inc., 1430 N. West Blvd., Vineland, N.J. 08360, as part number 5848-31. However, many inexpensive, chemically inert, non-dissolving, non-etchable materials other than glass could be used for the filter.

Filter 12 is held in place at the top of lower recess section 26 by filter retaining part 14. which is generally cylindrical in shape. Part 14 is designed to be press-fitted into the recess section 26 and is securely held in place by friction. Thus, the upper surface of filter 12 forms the floor of upper recess section 24. It functions to support the sample and to prevent solids from entering the lower recess section 26.

Part 14 may be made of Delrin, Azetel, Teflon or other solvent resistant plastic. Part 14 has an internal axial channel 28 with an upper filter disc receiving channel section 28a and a lower channel section 28b. Channel section 28b serves to permit access to the lower surface of filter 12, through recess section 26 of insert A.

Insert A is received in an opening 16 in housing B. Opening 16 is generally cylindrical, being adapted to receive insert body 10 therein.

Insert body 10 has a radially outwardly extending flange 30 which forms a portion of its upper surface. Opening 16 in housing B has an internal circumferential groove 32 adjacent its upper surface. Groove 32 receives flange 30 so as to properly seat the insert in the housing opening.

Figure 2:
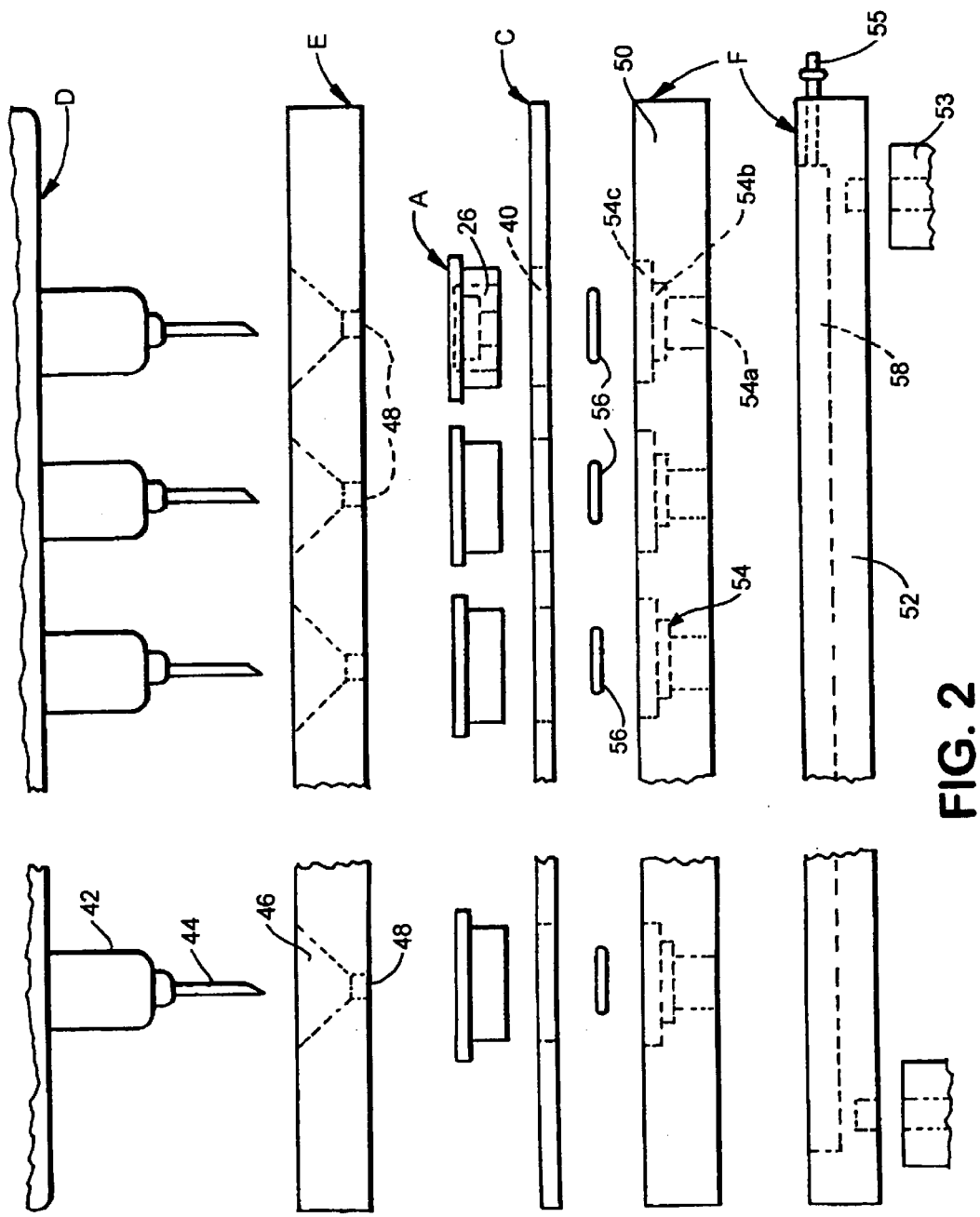
FIG. 2 is an exploded cross-sectional view of a multiple insert housing, funnel plate and vacuum plate.
Figure 3:
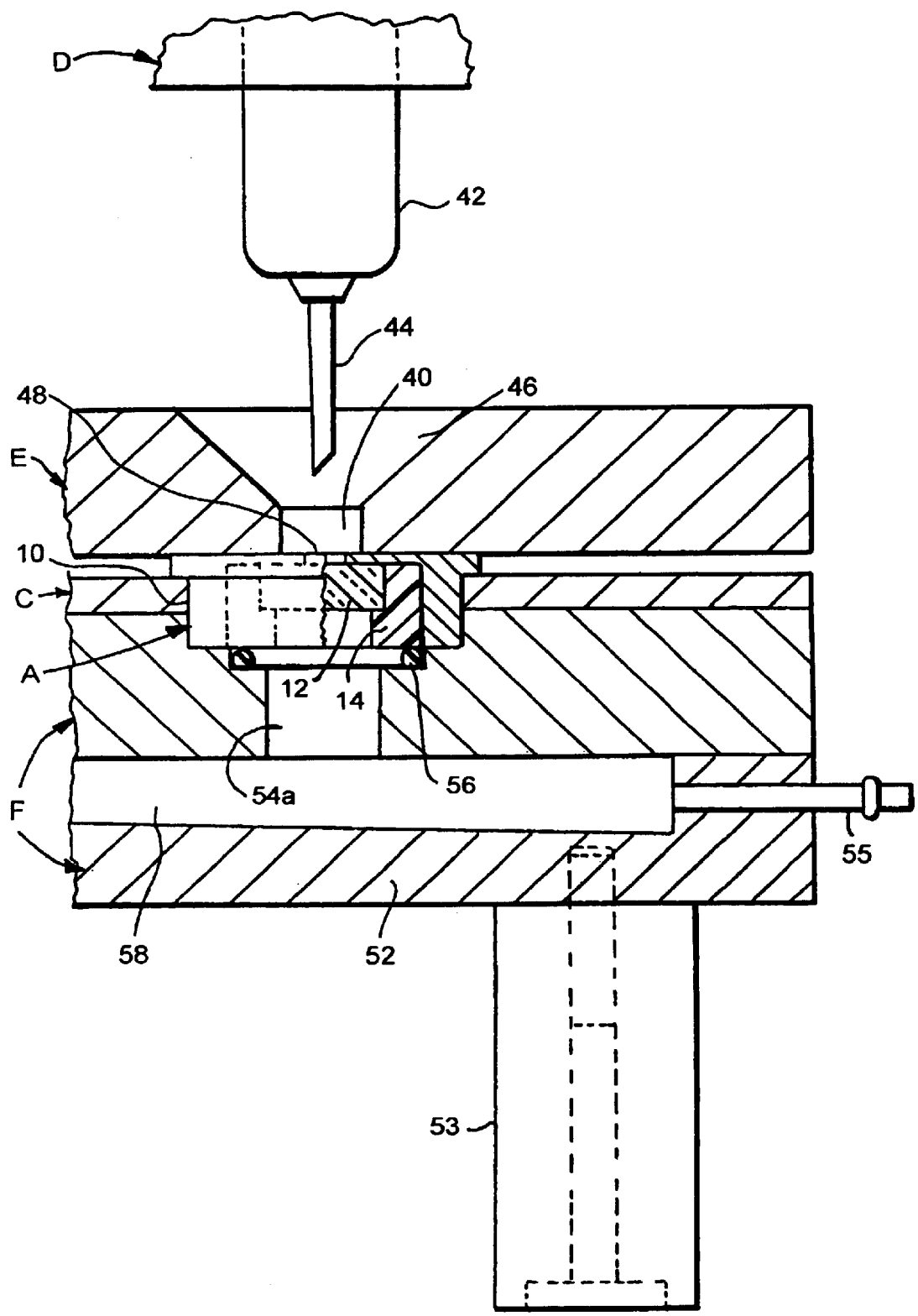
FIG. 3 is a cross-sectional side assembly view of a typical portion of the apparatus illustrated in FIG. 2.

FIG. 2 and 3 illustrate a second preferred embodiment of the present invention which includes a plurality of inserts A and a rectangular housing, generally designated C, designed for automated analysis of multiple pharmaceutical compounds by powder X-ray diffraction. Housing C has an array of openings 40 for receiving inserts A.

Samples of the compounds to be analyzed are introduced in slurry form into the upper recess 24 section (shown in FIG. 1) of each of the inserts A in housing C by a conventional liquid handler, generally designated D, such as a Gilson 215 Multiprobe Liquid Handler, through a funnel plate, generally designated E. Liquid handler D has a plurality syringe-like dispensing units 42 with needles 44. Each needle 44 aligns with a different one of a plurality of funnel shaped recesses 46 in funnel plate E.

Each funnel recess 46 in plate E has an outlet port 48 which aligns with the recess 24 in a different one of the inserts A. Thus, a sample containing a slurry of each of the compounds to be analyzed can be simultaneously introduced into each insert through the funnel plate.

In order to remove the liquid portion of each sample containing slurry, a pressure differential is created over the filters in each of the inserts simultaneously. This could be accomplished by applying pressure from above each filter using an inert gas, such as nitrogen. However, it is preferred to use a vacuum which is connected to the lower surface of each filter through the lower recess section of each insert.

In order to accomplish this, housing C, which carries multiple inserts A, is situated above a vacuum manifold, generally designated F, consisting of an upper vacuum plate 50 and a lower vacuum plate 52. Lower plate 52 is supported on legs 53.

Plate 50 has a plurality of ports 54, one for each insert A in housing C. Each port 54 has a lower section 54a which extends to the bottom surface of the plate, a sealing ring receiving section 54b and an upper section 54c adapted to receive the lower portion of the aligned insert A. A sealing ring in the form of an O-ring 56 is received in each section 54b adjacent to the bottom of the aligned insert, specifically, filter retaining part 14 of the insert. O-ring 56 supports part 14 (shown in FIG. 1), preventing filter 12 from changing position as the vacuum is applied through port 54. O-ring 56 also serves to seal the bottom of insert A to plate 50, when the insert is seated in port section 54c.

Lower vacuum plate 52 includes a channel 58 that is connected to a vacuum source through a nozzle 55. The vacuum is connected to each port 54 in plate 50 through channel 58 in plate 52. In this way, the vacuum is connected to the recess 26 in each insert A.

The internal axial channel 28b in each part 14 provides access to the bottom surface of filter 12 in each insert such that the vacuum acts on each filter. The vacuum simultaneously draws liquid from the slurry contained in recess section 24 of each insert, leaving the compound in powder form on the upper surface of the filter, filling recess section 24 with solids.

After filtration, the solids remaining in recess section 24 of each insert are washed and then dried. One way to accomplish this is to introduce a washing solution via the insert recesses and then draw the solution through the samples in the same manner as the original filtration. The entire assembly is then placed in a vacuum oven for drying prior to being placed in the X-ray diffractometer.

Preferably, recess 24 is from $\frac{1}{16}$" to $\frac{1}{8}$" in diameter. Recess 24 is very shallow, preferably only about 0.03 inch in depth. Approximately 0.25 milliliters of the sample containing slurry is received in the recess. After the liquid is removed, about 10 milligrams of powder remains in a very thin layer on the top surface of the filter. Even that small amount of sample has yielded acceptable results in the X-ray diffractometer (peak-to-noise ratio of 15.5 to 1). However, it is believed that amounts as small as 2 milligrams of powder would allow for successful analysis in a recess of those dimensions.

Figure 4:
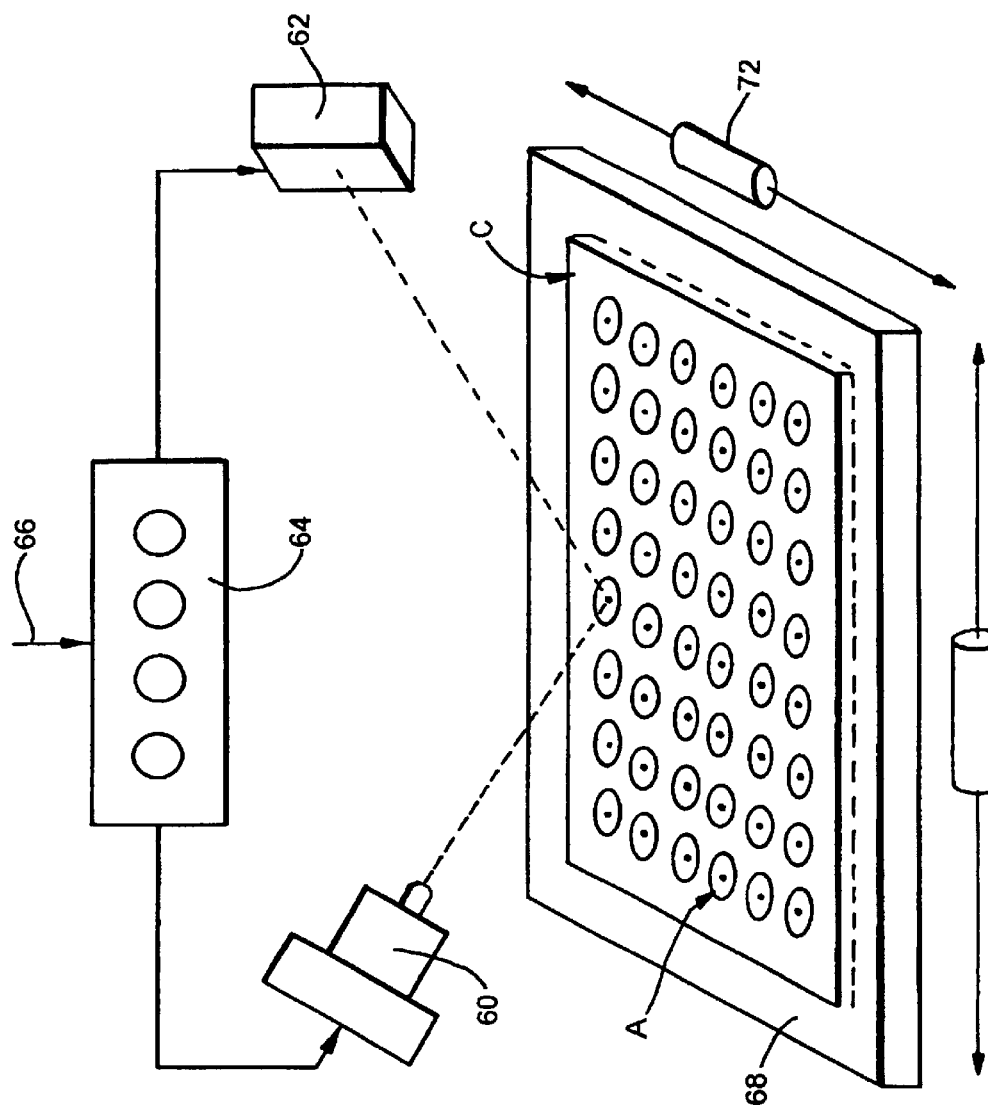
FIG. 4 is an schematic view of a X-ray diffractometer with the housing of FIG. 2.

FIG. 4 shows, in schematic fashion, how housing C, which carries an array of inserts A having samples in powder form, would be used in an X-ray diffractometer. The X-ray diffractometer consists of a focused X-ray source or tube 60 and a counter tube 62 connected to a count rate meter (not shown), all of which are controlled by a computer 64. Computer 64 has an electronic data entry port 66 which receives data relating to the parameters of the process used to prepare the sample compounds in each of the inserts.

Housing C is received in the recess of a platform 68. The platform can be moved in the X-Y plane by motors 70, 72, under control of computer 64. Housing C is magnetic or includes at least a section which is magnetized. The X-ray diffractometer will not function unless the housing is detected in the proper position on platform 68.

Each insert A in turn is scanned by the X-ray diffractometer. The resulting diffraction pattern is detected in conventional fashion and information as to the detected pattern is fed to computer 64. Computer 64 analyzes the diffraction patterns to determine the crystalline structure of the samples. It uses the laboratory data to deduce the production parameters which result in the desired polymorph forms.

It should now be understood that the present invention relates to a high throughput X-ray diffraction filtration sample holder assembly which eliminates manual handling of the samples in powder form, reducing sample loss inherent in such handling, and permits very small samples of multiple drug candidates to be screened in an automated fashion. Additionally, the invention allows parallel filtration of multiple samples with or without the use of an automated liquid handler, as well as the processing of individual samples.

While only a limited number of preferred embodiments of the present invention have been disclosed herein for purposes of illustration, it is obvious that many variations and modifications could be made thereto. It is intended to cover all of these variations and modifications which fall within the scope of the present invention, as defined by the following claims.

We claim:

1. A process for the X-ray diffraction analysis of a compound comprising:

a) preparing a sample of the compound to be analyzed in slurry form;

b) transferring the slurry to an assembly for a X-ray diffraction analysis, the assembly including a housing with an opening and an insert received in the housing opening, the insert having a recess for receiving the sample and a filter situated in the recess such that the filter supports the sample;

c) creating a pressure differential across the filter to remove the liquid portion of the slurry while the insert is in the housing opening and thereby obtain the sample to be analyzed in powder form in the insert recess;

d) transferring the assembly into a X-ray diffractometer; and e) performing X-ray diffraction analysis on the sample in the insert recess.

2. The process of claim 1 wherein the step of transferring the slurry comprises introducing the slurry into the insert recess.

3. The process of claim 1 wherein the step of creating a pressure differential comprises applying a vacuum to the filter through the insert recess.

4. The process of claim 1 wherein the step of creating a pressure differential comprises applying pressure to the filter through the insert recess.

5. The process of claim 1 wherein the step of receiving the insert in the housing opening comprises placing the insert into the housing opening from above the upper surface of the housing.

6. The process of claim 5 wherein the step of placing the insert comprises seating the insert within the housing opening.

7. An automated process for the X-ray diffraction analysis of multiple compounds comprising:

a) preparing samples of the compounds to be analyzed in slurry form;

b) transferring each slurry to an assembly for retaining a X-ray diffraction analysis sample, the assembly including a housing with an array of openings and multiple inserts, one insert for each sample, each insert being received in a different housing opening, each insert having a recess for receiving the sample and a filter situated in the recess such that the filter supports the sample;

c) while the inserts are in the housing, creating a pressure differential across each filter to remove the liquid portion of the slurry, leaving each sample to be analyzed in powder form in the insert recess;

d) transferring the assembly into a X-ray diffractometer; and e) performing X-ray diffraction analysis in sequence on each of the samples situated in the insert recesses.

8. The process of claim 7 wherein the step of preparing the compounds to be analyzed comprises preparing an array of samples in a multi-well reactor.

9. The process of claim 7 wherein the step of transferring the compounds comprises introducing each sample in slurry form into the recess of a different insert.

10. The process of claim 9 wherein the step of introducing each sample in slurry form comprises depositing said sample with an automated liquid handler.

11. The process of claim 7 wherein the step of creating a pressure differential comprises simultaneously applying a vacuum to each filter through the recess in each insert.

12. The process of claim 7 wherein the step of creating a pressure differential comprises simultaneously applying pressure to each filter through the recess in each insert.

13. The process of claim 7 further comprising the steps of generating laboratory information data for each of the multiple samples to be analyzed and utilizing the data in the X-ray diffraction analysis.

14. In combination a X-ray diffraction sample housing and an insert for use therewith, said housing having an opening for receiving said insert, said insert comprising a recess extending through said insert and a filter, said recess being formed to receive a sample of the compound to be analyzed in slurry form; and means for retaining the filter in the recess.

15. The combination of claim 14 wherein the recess comprises a section for receiving the sample and a second section within which the filter is retained.

16. The combination of claim 14 wherein the filter-retaining means comprises a channel providing access to the filter through the recess.

17. The combination of claim 14 for use with means for creating a pressure differential across the filter.

18. The combination of claim 14 wherein said insert is cylindrical in shape.

19. The combination of claim 14 wherein said insert is disc-shaped.

20. An X-ray diffraction analysis filtration sample assembly comprising an insert; a housing comprising means for interacting with a X-ray diffractometer and having an opening for receiving the insert, the insert having a recess extending therethrough and means for cooperating with the housing, said recess being formed to receive a sample of the compound to be analyzed in slurry form, and a filter; and means for retaining the filter in the recess.

21. The assembly of claim 20 wherein the means for cooperating with the housing comprises a flange on said insert and additional means on the housing to support the flange.

22. Apparatus for automated X-ray diffraction analysis of multiple compounds, comprising X-ray diffractometer means, multiple inserts and a housing with an array of openings into which said inserts are received; each insert comprising a recess extending therethrough, each of said recesses being formed to receive a sample of the compound to be analyzed in slurry form, a filter, and means for retaining the filter in the recess to support the sample; said housing being adapted to be received in said X-ray diffractometer means.

23. The apparatus of claim 22 wherein the inserts are removable from the housing.

24. The apparatus of claim 22 wherein the inserts are integrally formed in the housing.

25. The apparatus of claim 22 wherein the recess comprises a section for receiving the sample in slurry form and a second section within which the filter is retained.

26. The apparatus of claim 22 further comprising automated liquid handler means for introducing the samples in slurry form into the recess of each of the inserts.

27. The apparatus of claim 22 further comprising funnel means for facilitating introduction of the samples into the insert recesses.

28. The apparatus of claim 22 wherein the filter retaining means comprises channel providing access to said filter through the recess.

29. The apparatus of claim 22 wherein the X-ray diffractometer means comprises means for moving the housing relative to said X-ray diffractometer means to align each of the inserts, in sequence, with the X-ray diffractometer means.

30. The apparatus of claim 22 further comprising means for generating electronic data representative of each sample and for transferring the data to the X-ray diffractometer means.

31. The apparatus of claim 29 wherein the alignment means positions the inserts in relation to the X-ray diffractometer means according to two-dimensional coordinates.

32. The apparatus of claim 29 wherein the alignment means detects the presence of the inserts in the housing via a magnetic sensing means.

33. Apparatus for introduction and filtration of an array of samples of multiple compounds comprising a X-ray diffractometer and an array of X-ray diffraction analysis filter sample inserts, each insert including a recess which extends through the insert for receiving a sample of a compound in slurry form and a filter situated in the recess that supports the sample, said apparatus comprising a housing adapted to be received in said X-ray diffractometer, the housing comprising a plurality of openings into which the inserts are received, a funnel plate situated above said housing comprising a plurality of funnel shaped recesses each of which is aligned with the recess of a different one of the inserts and a vacuum plate located below said housing comprising a plurality of ports each of which is aligned with the recess of a different one.

34. Apparatus for automated X-ray diffraction analysis of multiple compounds, comprising X-ray diffractometer means, multiple inserts and a housing with an array of openings into which said inserts are received; each insert comprising a recess extending therethrough, each of said recesses being formed to receive a sample of the compound to be analyzed in slurry form, a filter, and means for retaining the filter in the recess to support the sample; said housing being adapted to be received in said X-ray diffractometer means, wherein the inserts are integrally formed in the housing.

* * * * *

UNITED STATES PATENT AND TRADEMARK OFFICE
CERTIFICATE OF CORRECTION

| | | |
|---|---|---|
| PATENT NO. | : 6,968,037 B2 | Page 1 of 1 |
| APPLICATION NO. | : 10/410910 | |
| DATED | : November 22, 2005 | |
| INVENTOR(S) | : Rosso et al. | |

It is certified that error appears in the above-identified patent and that said Letters Patent is hereby corrected as shown below:

Title page, Item (75), Inventors should read:

-- Victor W. Rosso
Glen Young
Joseph Nolfo
Imre M. Vitez
John J. Venit --

Signed and Sealed this

Twelfth Day of June, 2007

JON W. DUDAS
*Director of the United States Patent and Trademark Office*